United States Patent [19]

Adams et al.

[11] Patent Number: 4,952,875
[45] Date of Patent: Aug. 28, 1990

[54] EDDY CURRENT PROBE WITH RECESSES TO HOLD COILS AND ALLOW THE COILS TO ROCK AND MOVE PERPENDICULAR TO THE LONGITUDINAL AXIS OF THE PROBE

[75] Inventors: Helmar Adams; Georg Boegelein, both of Erlangen; Heinz Jacob, Memmelsdorf, all of Fed. Rep. of Germany

[73] Assignee: Siemens Aktiengesellschaft, Munich, Fed. Rep. of Germany

[21] Appl. No.: 366,161

[22] Filed: Jun. 14, 1989

[30] Foreign Application Priority Data

Jun. 15, 1988 [DE] Fed. Rep. of Germany ....... 3820423

[51] Int. Cl.$^5$ ...................... G01N 27/72; G01N 27/82
[52] U.S. Cl. ...................................... 324/220; 324/226
[58] Field of Search .............................. 324/219–221, 324/227, 226

[56] References Cited

U.S. PATENT DOCUMENTS

| | | | |
|---|---|---|---|
| 3,100,281 | 8/1963 | Spanner | 324/233 |
| 3,906,358 | 9/1975 | Stone . | |
| 3,916,302 | 10/1975 | Madewell | 324/220 |
| 4,303,884 | 12/1981 | Malick . | |

FOREIGN PATENT DOCUMENTS

| | | |
|---|---|---|
| 0242947 | 10/1987 | European Pat. Off. . |
| 2837486 | 10/1985 | Fed. Rep. of Germany . |
| 2250994 | 6/1975 | France . |
| 8604413 | 7/1986 | World Int. Prop. O. . |

OTHER PUBLICATIONS

Patent Abstracts of Japan, vol. 7, No. 96 (P-193) [1241], Apr. 22, 1983; and JP-A-5822951 (Mitsubishi Jukogyo K.K.), Feb. 10, 1983; Thu Summary is Pertinent.

Primary Examiner—Reinhard J. Eisenzopf
Assistant Examiner—Walter E. Snow
Attorney, Agent, or Firm—Herbert L. Lerner; Laurence A. Greenberg

[57] ABSTRACT

A device for eddy current testing of tubes of a heat exchanger having a U-shape tube bundle includes a test sensor having an insertion tip and a longitudinal axis. Elastic hose pieces are connected to the insertion tip. At least three coils are disposed along the elastic hose pieces. A pusher hose is connected to the elastic hose pieces. A pusher device is connected to the pusher hose for inserting the pusher hose into a tube of a tube bundle. The coils have contact surfaces each extending over only a portion of the inner periphery of the tube of the tube bundle. The coils are staggered about the circumference of the test sensor and are staggered along the longitudinal axis of the test sensor. A location recognition unit is disposed in the test sensor.

11 Claims, 3 Drawing Sheets

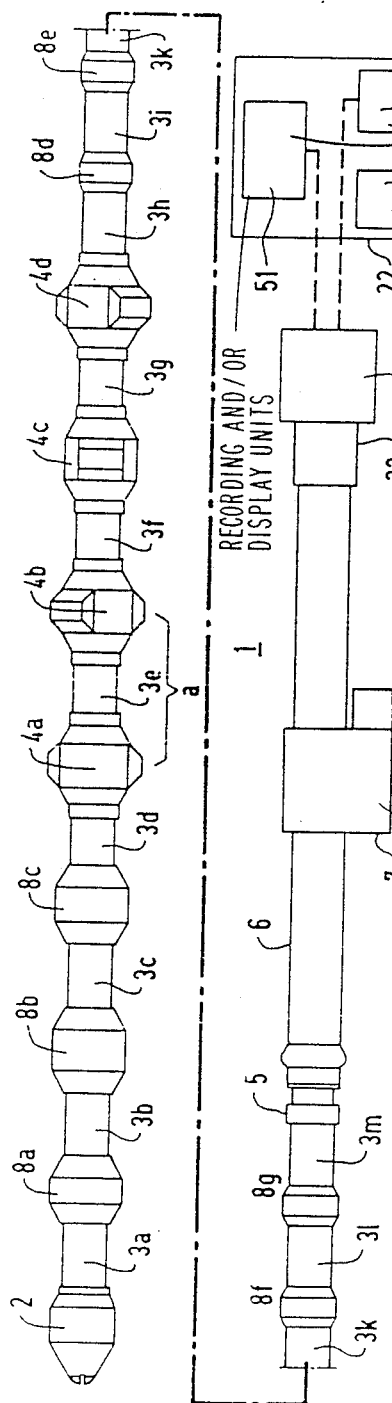
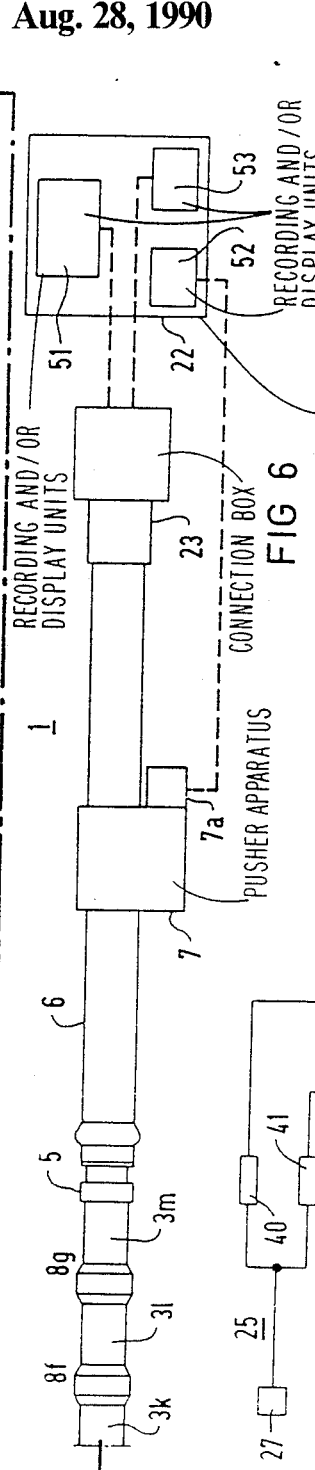
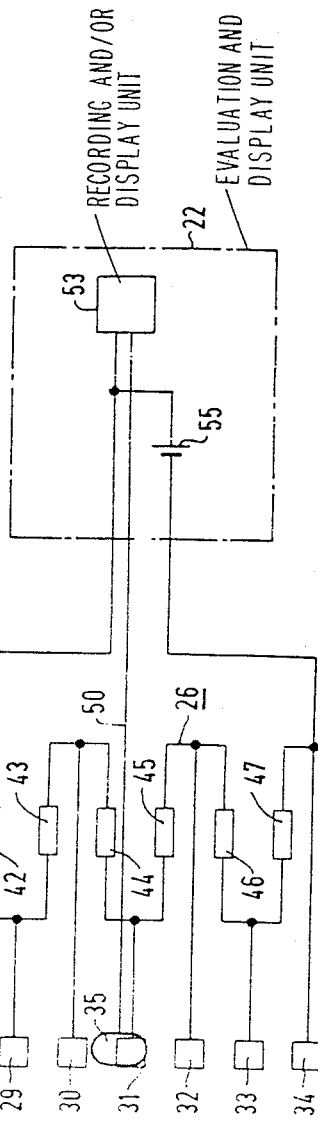
FIG 6
FIG 7

EDDY CURRENT PROBE WITH RECESSES TO HOLD COILS AND ALLOW THE COILS TO ROCK AND MOVE PERPENDICULAR TO THE LONGITUDINAL AXIS OF THE PROBE

The invention relates to a device for eddy current testing and can be used to test the tubes of a heat exchanger having a U-shaped tube bundle or nest.

German Patent DE No. 28 37 486 C3 discloses a device for eddy current testing in which a test sensor is provided that has toroidal coils which are disposed in two parallel planes transverse to the tube axis and are embedded in a coil core. One end of the test sensor is connected to a pusher hose through a flexible hose carrying a guide body, and the other end is connected to an insertion tip through another flexible hose carrying a guide body. The flexible hoses have greater flexibility than the pusher hose, through which the test sensor can be inserted into a tube of the U-shaped tube bundle by means of a pusher apparatus. In that known structure, the two coil axes are coaxial with the longitudinal axis of the test sensor on the coil core. Thus, although flaws in the tube to be tested can be found in both the straight and curved parts of the tube, nevertheless it is impossible to locate the precise location along the circumference of the tube.

Another eddy current sensor is known in which a coil has a contact surface that extends over only a portion of the inner periphery of the tube to be tested. In such a device, the sensor must be made to rotate, in order to scan the tube.

U.S. Pat. No. 4,303,884 discloses an eddy current sensor that has a great number of axially extending, elastic plastic strips, which form the periphery of the test head. One coil for eddy current testing is secured to each strip. In that construction, it is unnecessary to rotate the sensor, because during the insertion motion, the entire inner surface of the tube to be tested is swept by the coils. However, such a known device is only suitable for testing straight tubes. Furthermore, the location of a flaw is only indicated by a length measurement, so that the only conclusion that can be drawn is the height at which the flaw in the tube is located.

It is accordingly an object of the invention to provide a device for eddy current testing of the tubes of a heat exchanger, which overcomes the hereinafore-mentioned disadvantages of the heretofore-known devices of this general type and with which the location of a flaw can not only be determined in the curved part of a tube of a heat exchanger by a length measurement but also by an angular measurement. In other words, the site of the flaw can also be determined along the circumference of the tube to be tested. In order to evaluate the eddy current testing and the actions to be taken, it is desirable to be able to ascertain the precise location of a flaw in the tube, so as to conclude as accurately as possible what the cause of the flaw might be. One important factor, for instance, is whether or not the flaw is located at a support point of the tube of a tube bundle. Supports of this kind are also provided in the curved portion of the tube bundle of a heat exchanger.

With the foregoing and other objects in view there is provided, in accordance with the invention, a device for eddy current testing of tubes of a heat exchanger having a U-shaped tube bundle, comprising a test sensor having an insertion tip and a longitudinal axis, elastic hose pieces connected to the insertion tip, at least three coils disposed along the elastic hose pieces, a pusher hose connected to the elastic hose pieces, a pusher device connected to the pusher hose for inserting the pusher hose into a tube of a tube bundle, the coils having contact surfaces each extending over only a portion of the inner periphery of the tube of the tube bundle, the coils being staggered about the circumference of the test sensor and being staggered along the longitudinal axis of the test sensor, and a location recognition unit disposed in the test sensor.

In this way, flaws can be detected even in portions of a U tube with a short radius of curvature, by making a length and an angle measurement.

In accordance with another feature of the invention, the test sensor has coil holders with recesses formed therein perpendicular to the longitudinal axis of the test sensor, and springs disposed in the recesses for displaceably supporting the coils.

In accordance with a further feature of the invention, each of the coils have two coil carriers disposed in one of the recesses for supporting the coils.

In accordance with an added feature of the invention, the test sensor has four recesses formed therein being staggered along the longitudinal axis of the sensor and staggered about the circumference of the test sensor by an angle of 45°, and there are provided two coil carriers disposed in each respective recess for supporting the coils, the contact surfaces of the coils being overlapped.

In accordance with an additional feature of the invention, there are provided printed circuit boards supported in the coil holders and electrically connected to the coils.

In accordance with yet another feature of the invention, the elastic hose pieces are hollow shaft segments, and there are provided supports or guide bodies disposed along the hollow shaft segments, the supports and the coil holders having central through openings formed therein and extensions on both ends thereof with female threads for screwing-in the hollow shaft segments.

In accordance with yet a further feature of the invention, the location recognition unit is an electrical resistor network having a plurality of pickups and contacts connected to the pickups, the contacts being disposed at equal intervals in the test sensor, such as on the inner periphery of one of the hollow supports, and there is provided a rope or cable fastened tautly in the test sensor, a contact body, such as a contact ball, disposed on the rope and associated with the contacts, electrical lines connected to the contact body, and an evaluation unit connected to the electrical lines.

In accordance with yet an added feature of the invention, there is provided a connection box for the pusher hose, the rope having one end secured at the insertion tip and another end secured to the connection box, and a tension spring connected to the rope.

In accordance with a concomitant feature of the invention, the coil carriers have axial tangs disposed parallel to the longitudinal axis of the test sensor, the tangs being resiliently and displaceably supported in radial slits formed in the coil holders.

Other features which are considered as characteristic for the invention are set forth in the appended claims.

Although the invention is illustrated and described herein as embodied in a device for eddy current testing of the tubes of a heat exchanger, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

FIG. 6 is an exploded side-elevational view of a device for eddy current testing, on a smaller scale than FIG. 1;

FIG. 7 is a schematic electrical circuit diagram of a location recognition unit of the sensor;

Figure 1:
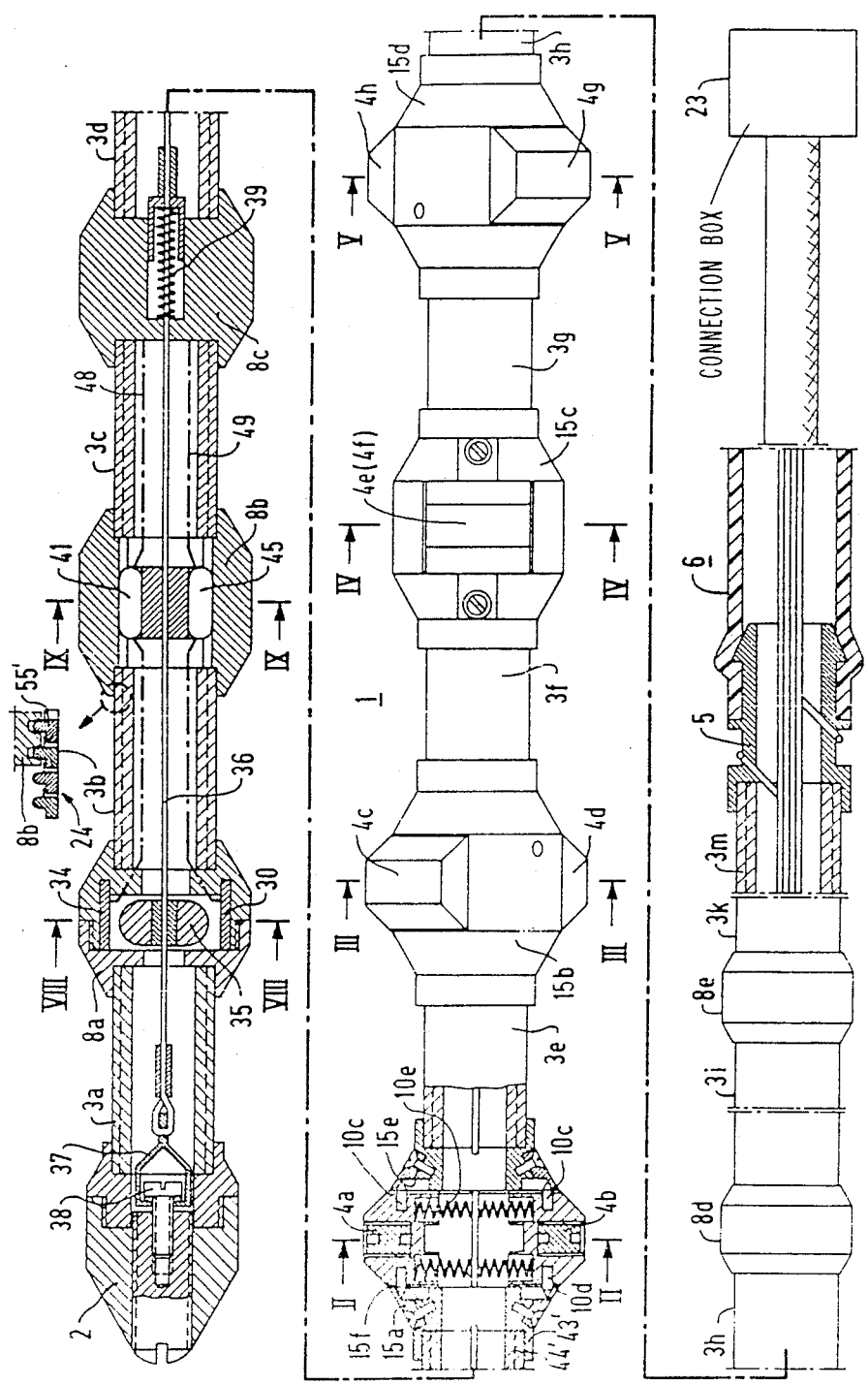
FIG. 1 is an exploded, fragmentary, diagrammatic, longitudinal-sectional view of an eddy current sensor on an enlarged scale.

Referring now to the figures of the drawing in detail and first, particularly, to FIGS. 1 and 6 thereof, there is seen a device for eddy current testing of the tubes of a heat exchanger having a U-shaped tube bundle, that is formed of a test sensor 1, in which an insertion or introduction tip 2 is connected through elastic hose pieces 3a–3m, having supports 8a–8g and coils 4a–4h therebetween, to a coupler 5 constructed in the form of a plug-in element. A pusher hose 6 which is connected to the coupler 5, is thrust into one tube of the U-shaped tube bundle by means of a pusher apparatus 7. The elastic hose pieces 3a–3m, which are more flexible than the pusher hose 6, are guided in the tube to be tested by the supports 8a–8g, which are annular in construction.

Figure 2:
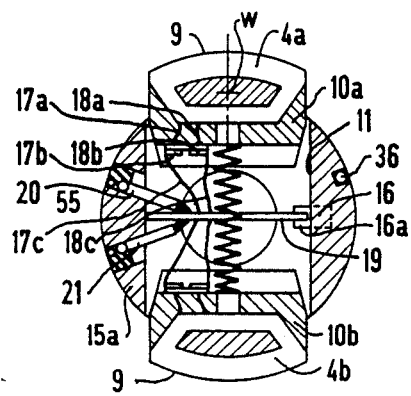
FIGS. 2-5 are cross-sectional views taken along the lines II—II through V—V, respectively, in FIG. 1, in the direction of the arrows.
Figure 3:
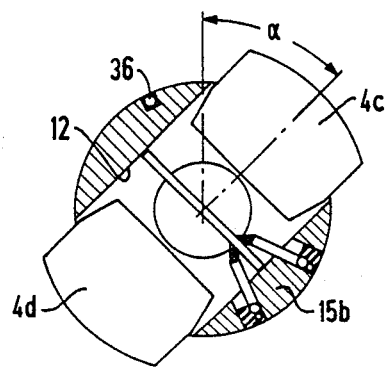
Figure 4:
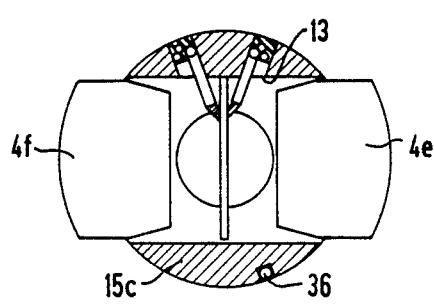

FIG. 1 together with FIGS. 2-7 show that contact surfaces 9 of the coils 4a–4h which are shown in FIGS. 2, each extend over only a portion or sector of the outer periphery of the sensor 1, or of the inner periphery of the tube to be tested. The coils 4a–4h are offset from one another or staggered about the circumference of the sensor 1 by predetermined angles alpha as shown in FIGS. 2 and 3 as well as by a length a shown in FIG. 6 in the longitudinal axis of the sensor, so that as the sensor 1 is pushed through the tube to be tested, each coil 4a–4h scans a given portion of the inner surface of the tube. A winding axis w of the coils 4a–4h is perpendicular to the plane of the drawing in FIG. 2, so that the coils are disposed parallel to the sensor axis and are at least partly embedded in coil carriers 10a, 10b. The coil carriers 10a, 10b are movably disposed in recesses 11-14 disposed at right angles to the sensor axis in coil holders 15a–15d shown in FIGS. 2-5. The coil carriers 10a, 10b have axial tangs 10c, 10d shown in FIG. 1, which are disposed parallel to the sensor axis, so as to allow both a rocking motion and a vertical motion and to this end are displaceably supported in radial slits 15e, 15f in the coil holders 15a–15d. This permits good adaptation of the contact surfaces 9 of the coil to the inner surface of the tube, even at curved parts of the tube. The coil carriers 10a, 10b are pressed outward into the recesses 11-14 through springs 10e.

In the illustrated exemplary embodiment, two coil carriers 10a, 10b are each resiliently disposed in one recess with one coil. Accordingly, the sensor 1 has four recesses 11-14, which are offset or staggered along the longitudinal axis of the sensor, each having two coil carriers such as 10a, 10b, and the recesses 11-14 are offset from one another or staggered by an angle alpha=45°, so that the contact surfaces 9 of the coils 4a–4h overlap one another.

Ends 17a, 18a of lines of the coils are carried to connection points 17b, 18b on the coil carrier, as shown in FIG. 2. From there, movable wires 17c, 18c lead to electrical printed circuit or wiring boards 19, which are retained in the interior of the coil holders 15a–15d by pins 16 having slits 16a. Two electric cables 20, 21 lead from each printed circuit board 19 to conduits in the coil holders, and from there they lead through the interior of the elastic hose pieces 3e–3m shown in FIG. 1 and through the pusher hose to a connection box 23, or to the coupler 5 and from there through the pusher hose 6 to the connection box 23, which is connected to an evaluation and display unit 22 shown in FIG. 6.

Figure 8:
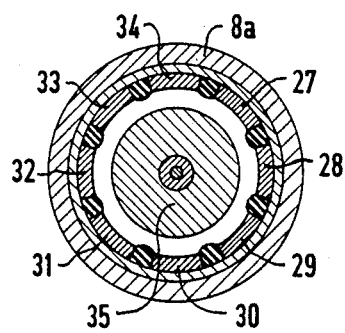
FIG. 8 is a cross-sectional view taken along the line VIII—VIII in FIG. 1, in the direction of the arrows, showing the contact configuration of the location recognition unit.
Figure 9:
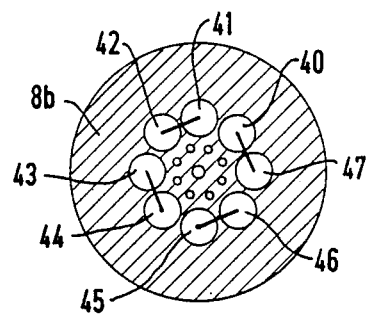
FIG. 9 is a cross-sectional view taken along the line IX—IX in FIG. 1, in the direction of the arrows, showing the disposition of the resistors.

In order to locate a flaw, a location recognition unit 25 is provided in the sensor 1. As FIGS. 7, 8 and 9 show, the position recognition unit 25 is made up of an electrical resistor network 26 having a plurality of pickups connected to contacts 27-34. The contacts 27-34 are spaced apart at equal intervals on the inner periphery of a two-piece hollow support 8a shown in FIG. 8, with insulating elements disposed therebetween. A contact body 35 shown in FIGS. 1, 7 and 8 in the form of a spherical body, is associated with the contacts 27-34 and is floatingly retained along the sensor axis on a rope or cable 36 fastened tautly in the sensor 1. One end of the rope 36 is secured in the interior of the introduction tip 2 by means of a stirrup 37 held by a screw 38 and the rope is guided through the supports 8a–8e and accommodated in conduit on the coil holders as shown in FIGS. 2-5. The other end of the rope 36 is anchored at the coupler 5 for the pusher hose 6, and from there is optionally guided through the pusher hose to the connection box 23 shown in FIG. 1. In order to keep the rope 36 taut at all times, a tension spring 39 is disposed in one of the supports or guide bodies 8c. The resistors 40-47 of the resistor network 26 are likewise accommodated in the hollow space of a support 8b. The evaluation and display unit 22 is equipped with display and/or recording devices 51, 52, 53 shown in FIG. 6. The resistor network 26 is connected to the evaluation and display unit 22 through electric lines 48, 49 and the contact body 35 is connected to the evaluation and display unit 22 through an electric line 50.

The eddy current test results are displayed graphically in the recording unit 51, which has an oscillograph screen. The pusher apparatus or device 7 is provided with a counter mechanism 7a, from which electrical lines lead to the display unit 51, which displays the length through which the sensor has been inserted into the tube to be tested.

Figure 5:
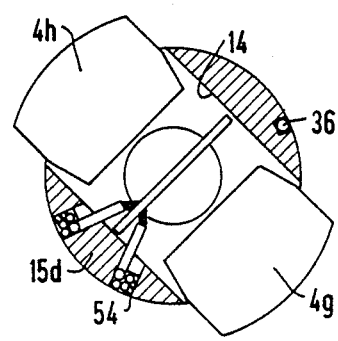

The lines 48-50 are run through the interior of the elastic hose pieces 3a–3m, and the lines 48-50 are accommodated together with the cables 20, 21 in conduits 54 shown in FIG. 5 at the coil holders 15a–15d. As FIG. 7 also shows, the electric lines 48, 49 are connected to a direct voltage source 55. The resistor network 26 forms a voltage divider having pickups at which defined voltages are present, such as with the values 2, 4, 6, 8, 10, 12, 14 and 16 Volts. If the sensor enters the curved zone of the tube to be tested, then the contact body 35 touches one of the contacts 27-34. Since the coils 4a-4h are definitively associated with the contacts 27-34, the location of the individual coils in the curve of the tube is thus certain. The voltage present between the lines 49 and 50 is a measure of the angular location of the various coils in the curve of the tube to be tested. The voltage value at a given time is detected by the recording unit 53 which is in the form of a voltage plotter.

Each of the elastic hose pieces 3a-3m disposed between the supports 8a-8e and the coils 15a-15d is in the form of a hollow shaft segment, which is substantially formed of a flexible wire helix 24 with radial interlocking of the helixes, as shown in the enlarged portion of FIG. 1 above the elastic hose piece 3b. The hollow shaft segments have helical ribs 55', which form a male thread. The supports 8a-8e and coil holders 15a-15d have a central passageway or through opening and extensions 43' at both ends with female threads 44' for screwing in the hollow shaft segments.

The accuracy in detection of the angular location of a flaw can be increased with the number of coils, if it is not sufficient to sweep circumferential angles of 45° with four pairs of coils, as shown for the exemplary embodiment. If the need for locating a flaw is not very stringent, however, then even fewer than four pairs of windings, such as three windings offset or staggered by 120°, may optionally suffice.

We claim:

1. Eddy current probe for testing tubes of a heat exchanger having a U-shaped tube bundle, comprising a test sensor having an insertion tip and a longitudinal axis, elastic hose pieces connected to said insertion tip, at least three coils being spaced apart along the longitudinal axis of said test sensor between said elastic hose pieces, a pusher hose connected to said elastic hose pieces, a pusher device connected to said pusher hose for inserting said pusher hose into a tube of a tube bundle, said coils having contact surfaces each extending over only a portion of the inner periphery of the tube of the tube bundle, said coils being mutually rotated in position about the circumference of said test sensor, a location recognition unit disposed in said test sensor, said test sensor having coil holders with means including recesses formed therein perpendicular to the longitudinal axis of said test sensor and springs disposed in said recesses for displaceably supporting and allowing said coils to rock and move perpendicular to said longitudinal axis of said test sensor.

2. Probe according to claim 1, wherein each of said coils have two coil carriers disposed in one of said recesses for supporting said coils.

3. Probe according to claim 1, wherein said test sensor has four recesses formed therein being staggered along the longitudinal axis of said sensor and staggered about the circumference of said test sensor by an angle of 45°, and including two coil carriers disposed in each respective recess for supporting said coils, said contact surfaces of said coils being overlapped.

4. Probe according to claim 1, including printed circuit boards supported in said coil holders and electrically connected to said coils.

5. Device Probe according to claim 1, wherein said elastic hose pieces are hollow shaft segments having male threads, and including supports disposed along said hollow shaft segments, said supports and said coil holders having central through openings formed therein and extensions on both ends thereof with female threads into which said male threads are screwed.

6. Probe according to claim 1, wherein said location recognition unit is an electrical resistor network having a plurality of pickups and contacts connected to said pickups, said contacts being disposed at equal intervals in said test sensor, and including a rope fastened tautly in said test sensor, a contact body disposed on said rope and associated with said contacts, electrical lines connected to said contact body, and an evaluation unit connected to said electrical lines.

7. Probe according to claim 6, wherein said contact body is in the form of a contact ball.

8. Probe according to claim 5, wherein said location recognition unit is an electrical resistor network having a plurality of pickups and contacts connected to said pickups, said contacts being disposed on the inner periphery of one of said supports, and including a rope fastened tautly in said test sensor, a contact body disposed on said rope and associated with said contacts, electrical lines connected to said contact body, and an evaluation unit connected to said electrical lines.

9. Probe according to claim 6, including a connection box for said pusher hose, said rope having one end secured at said insertion tip and another end secured to said connection box, and a tension spring connected to said rope.

10. Probe according to claim 8, including a connection box for said pusher hose, said rope having one end secured at said insertion tip and another end secured to said connection box, and a tension spring connected to said rope.

11. Probe according to claim 2, wherein said coil carriers have axial tangs disposed parallel to the longitudinal axis of said test sensor, said tangs being resiliently and displaceably supported in radial slits formed in said coil holders.

* * * * *